(12) United States Patent
Piterski et al.

(10) Patent No.: US 9,895,256 B1
(45) Date of Patent: Feb. 20, 2018

(54) INDWELLING URINARY CATHETER RETENTION APPARATUS

(71) Applicants: Brahm H Piterski, Saint Petersburg, FL (US); Paul J Piterski, Saint Petersburg, FL (US)

(72) Inventors: Brahm H Piterski, Saint Petersburg, FL (US); Paul J Piterski, Saint Petersburg, FL (US)

( * ) Notice: Subject to any disclaimer, the term of this patent is extended or adjusted under 35 U.S.C. 154(b) by 0 days.

(21) Appl. No.: 15/655,999

(22) Filed: Jul. 21, 2017

Related U.S. Application Data

(60) Provisional application No. 62/498,910, filed on Jan. 12, 2017.

(51) Int. Cl.
*A61M 25/00* (2006.01)
*A61M 25/02* (2006.01)
*A61F 5/453* (2006.01)
*A61M 25/01* (2006.01)

(52) U.S. Cl.
CPC ......... *A61F 5/453* (2013.01); *A61M 25/0017* (2013.01); *A61M 25/01* (2013.01); *A61M 2025/0206* (2013.01); *A61M 2025/0213* (2013.01)

(58) Field of Classification Search
CPC ....... A61F 5/453; A61F 5/4408; Y10S 128/26
See application file for complete search history.

(56) References Cited

U.S. PATENT DOCUMENTS

| 1,032,611 | A | * | 7/1912 | Keyes | A61M 25/02 128/DIG. 26 |
|---|---|---|---|---|---|
| 1,213,001 | A | * | 1/1917 | Philips | A61M 25/0606 128/207.29 |
| 2,409,432 | A | * | 10/1946 | Hubbard | A61M 25/02 128/DIG. 26 |
| 3,742,953 | A | * | 7/1973 | Lee | A61F 5/453 128/DIG. 15 |
| 3,957,048 | A | * | 5/1976 | Jacobs | A61M 25/02 128/DIG. 26 |
| 4,419,097 | A | * | 12/1983 | Rowland | A61F 5/453 604/174 |
| 4,516,968 | A | * | 5/1985 | Marshall | A61M 25/02 128/DIG. 26 |
| 4,519,793 | A | * | 5/1985 | Galindo | A61M 25/02 128/DIG. 26 |

(Continued)

OTHER PUBLICATIONS

Falls et al. "Indwelling Foley Catheters", Critical Care Nurse, vol. 25, No. 2, pp. 44-51, Apr. 2005, US.

(Continued)

*Primary Examiner* — Adam Marcetich
(74) *Attorney, Agent, or Firm* — David Kiewit

(57) ABSTRACT

An indwelling urinary catheter is subject to slipping out of a patient's bladder unless provisions are made for retaining it. Retention apparatus for use with a male patient provides a clamp bearing on the catheter, an anchor member attached to the male patient's penis and a linking member connecting the anchor and clamp so as to hold the clamp against the penis. A single-use intermittent catheter, in conjunction with the retention apparatus provides an indwelling catheter that does not require an intra-bladder balloon to hold it in place within the bladder.

7 Claims, 2 Drawing Sheets

(56) References Cited

U.S. PATENT DOCUMENTS

| | | | | |
|---|---|---|---|---|
| 4,971,074 | A * | 11/1990 | Hrubetz | A61F 2/0054 |
| | | | | 128/885 |
| 5,195,998 | A * | 3/1993 | Abraham | A61F 5/453 |
| | | | | 604/349 |
| 5,795,334 | A * | 8/1998 | Cochrane, III | A61M 25/02 |
| | | | | 128/DIG. 26 |
| 5,797,890 | A | 8/1998 | Goulter | |
| 6,298,851 | B1 * | 10/2001 | Parota | A61M 16/0472 |
| | | | | 128/207.29 |
| 8,858,536 | B1 | 10/2014 | Baratta | |
| 2010/0145314 | A1 * | 6/2010 | Hazan | A61M 25/02 |
| | | | | 604/544 |
| 2015/0352321 | A1 | 12/2015 | Hannon et al. | |
| 2017/0246435 | A1 * | 8/2017 | Oveland | A61M 25/02 |

OTHER PUBLICATIONS

Feneley et al., "An Indwelling Urinary Catheter for the 21st Century", Brit. J. Urol. Int., vol. 109, No. 12, pp. 1746-1749, Jun. 2012, GB.

Avulova et al., "Do Foley Catheters Adequately Drain the Bladder?", Int. Brazil. J. Urol., vol. 41. No. 3, pp. 552-555, May-Jun. 2015, BR.

\* cited by examiner

INDWELLING URINARY CATHETER RETENTION APPARATUS

BACKGROUND INFORMATION

A variety of medical conditions require draining a patient's bladder by inserting a catheter through the urethra into the bladder. In a simple case the catheter is a flexible tube having a single lumen. Absent a reliable retention arrangement, this catheter will slide out of the urethra and is hence commonly removed after each drainage. This single-use protocol provides a substantial risk of injury to and infection of both the urinary tract and the bladder.

The well-known Foley indwelling catheter is retained by a balloon at the proximal end of the catheter. The balloon is inflated through a first of two lumens, to a diameter greater than the urethra's. This retains the indwelling catheter and allows for continuous drainage through the second lumen. Because the second lumen is necessarily narrower than a single lumen in a catheter having the same outer diameter, drainage may be impeded. The very narrow drainage lumen can also clog, resulting in acute pain, and removal of the catheter. Moreover, the Foley catheter can fail to deflate resulting in an acutely painful forcible withdrawal of the still inflated balloon.

Thus, there is an unfulfilled need for an arrangement for retaining the proximal end of a urethral catheter in a patient's bladder without requiring a balloon or multiple lumens.

BRIEF SUMMARY OF THE INVENTION

One aspect of the invention is that it provides apparatus for inserting a urinary catheter having a selected diameter through a male patient's penis and for retaining a proximal portion of the inserted catheter in the bladder. The apparatus comprises a clamp member, an anchor member and at least one elongate linking member connecting the clamp to the anchor when the catheter is being retained. The clamp member preferably engages the catheter so as to prevent relative motion therebetween. The preferred anchor member is fitted around a shaft of the penis. Each elongate linking member has one end connectable to the clamp by a touch-responsive connector, such as a hook-and-loop fabric, and has a second end similarly connectable to the anchor sleeve.

Another preferred aspect of the invention is that it provides apparatus for inserting a urinary catheter having a selected diameter through a male patient's penis and for retaining a proximal portion of the inserted catheter in the patient's bladder. This apparatus comprises a clamp member; an anchor member and at least one link member. The preferred clamp member is selectively attachable to the catheter subsequent to the insertion thereof. The preferred anchor member comprises a flexible sheet wrappable about a shaft of the patient's penis to form a tubular anchor having, on its outer surface, a respective at least one touch-responsive bonding portion for connection to one end of the link member. The other end of the link member is similarly connectable to the clamp member.

Yet another aspect of the invention is that it provides a method of retaining a proximal end of a urinary catheter in a bladder of a male patient. An anchor is formed by wrapping a flexible member around the shaft of the patient's penis to form a sleeve held together by touch-responsive bonding portions, which may comprise cooperating portions of hook-and-loop fabric. At least one linking member is then attached between the anchor sleeve and a clamp that is attached to the catheter adjacent the patient's meatus. Touch-responsive bonding portions on the anchor, collar and linking members provide the physical connections. The lengths of the linking member or members are adjusted to hold the clamp member in abutting contact with the meatus of the patient's penis.

Those skilled in the art will recognize that the foregoing broad summary description is not intended to list all of the features and advantages of the invention. Both the underlying ideas and the specific embodiments disclosed in the following Detailed Description may serve as a basis for alternate arrangements for carrying out the purposes of the present invention and such equivalent constructions are within the spirit and scope of the invention in its broadest form. Moreover, different embodiments of the invention may provide various combinations of the recited features and advantages of the invention, and that less than all of the recited features and advantages may be provided by some embodiments.

DETAILED DESCRIPTION OF A PREFERRED EMBODIMENT

Figure 1:
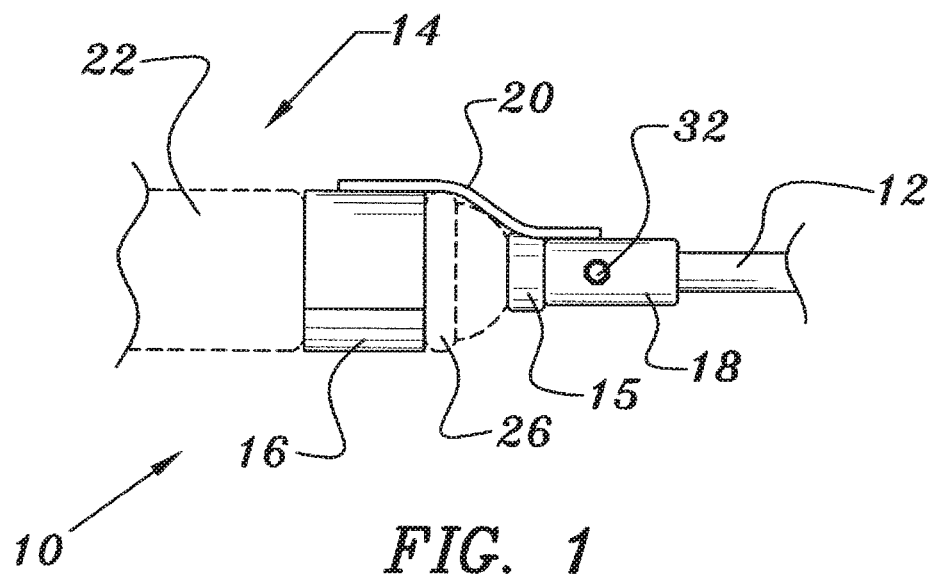
FIG. 1 is a partly schematic elevational view of preferred apparatus of the invention.
Figure 2:
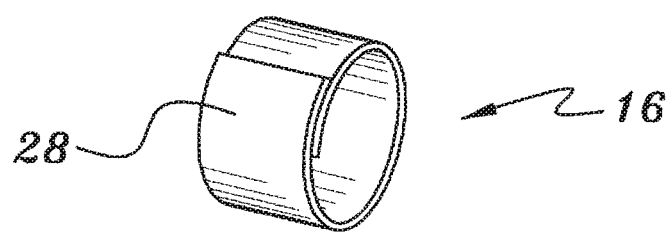
FIG. 2 is a perspective view of an anchor member in a rolled state.
Figure 3:
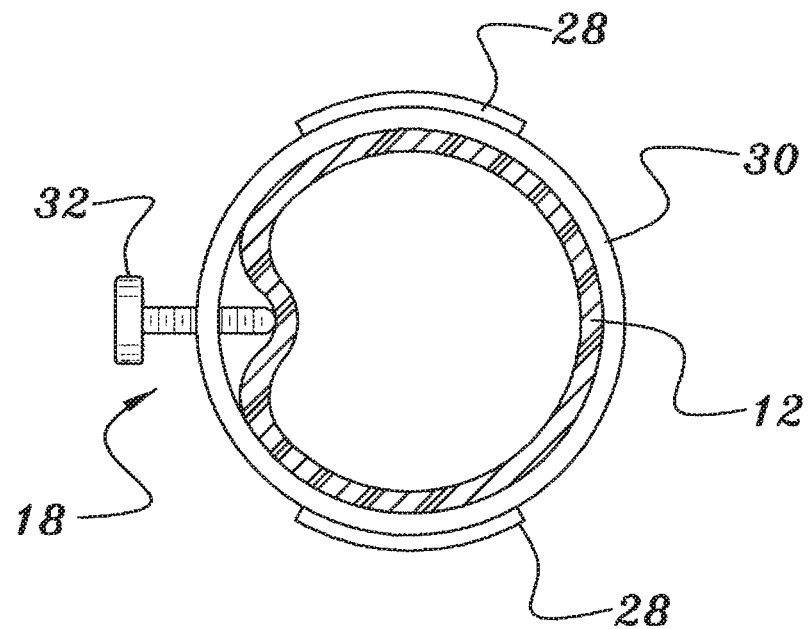
FIG. 3 is an end view of a clamp member having a thumb screw engaging a wall of a catheter.

In studying this Detailed Description, the reader may be aided by noting definitions of certain words and phrases used throughout this patent document. Wherever those definitions are provided, those of ordinary skill in the art should understand that in many, if not most, instances such definitions apply both to preceding and following uses of such defined words and phrases.

The terms 'proximal' and 'distal' provide location references defined with respect to a patient. Hence, it is the proximal end of a catheter that is inserted into a patient's bladder, and the distal end that connects to a urine collection reservoir.

The term 'touch-responsive bonding' refers to mechanical connections formed by touching one of the elements being connected to another. An example of touch responsive bonding is provided by hook and loop fasteners.

Many sorts of hook-and-loop bonding elements are known. These comprise fabrics having hooks on one side and loops on the other; adhesive-backed hook or loop material; and fabrics having patches of a selected hook or loop material attached in appropriate places. The reader may note that the type of bonding elements depicted in the drawing were generally selected for the sake of clarity of presentation and are not intended to limit the disclosure.

Turning now to FIG. 1, one finds a preferred catheter retaining apparatus 10 of the invention. A proximal end (not shown) of a catheter 12, which may be of any known variety, has been inserted through a male patient's penis 14 and into his bladder (not shown).

Retaining apparatus 10 of the invention preferably comprises an anchor member 16 attached to the male patient's penis, a clamp member 18 attached to a portion of the catheter adjacent the meatus of the penis 14 and one or more linking members 20 adjustably connecting the anchor 16 to the clamp 18.

In a preferred embodiment, the anchor member is disposed around the shaft 22 of the patient's penis. This anchor member 16 may be formed by wrapping a flexible fabric sheet around the penile shaft 22 to form a sleeve that preferably has a smooth fabric side against the patient's skin. Preferably, the anchor is wrapped snugly enough that a corona 26 of the patient's penis prevents a distal end of the anchor member from sliding off.

Patches of hook and loop fabric 28 are preferably used both to secure two sides of the sheet together to form the fitted sleeve and to attach one or more linking members 20 to the sleeve. The skilled reader will appreciate that although hook-and-loop fasteners are preferred, connection of the anchor to the linking member may also be provided by other touch responsive bonding apparatus.

In a preferred embodiment both the anchor 16 and the retaining clamp 18 have at least respective portions of their external surfaces covered with hook-type fabric. In a particular case both the anchor and the clamp have bondable portions about one and one-half inches in length. In this case the linking member may comprise a flexible sheet having at least a substantial fraction of at least one surface covered with loop-type fabric. Preferably, the linking member 20 is formed from hook-and-loop fabric 28 having hooks on one side and loops on the other. The reader will appreciate that one could also choose to have the loop material on the anchor and clamp and the hook material on the link member.

A preferred retaining clamp 18 comprises a plastic sleeve 30 having a thumb screw 32, preferably knurled, mounted in a threaded hole in the sleeve. Preferably, the plastic sleeve 30 has an inner diameter slightly greater than an outer diameter of a catheter 12 with which it is to be used. Moreover, the thumb screw 32 may be chosen to be long enough that it clamps the catheter firmly when fully turned into the hole, and also to be short enough that it cannot be turned in so far as to crush or damage the catheter.

In a particular preferred embodiment a cushioning member 15 that may be made from a soft rubber, plastic foam or other suitable material, is affixed to the proximal end of the clamp 18. This provides a cushion interposed between the clamp and the penis and may also provide a barrier to dirt and germs.

In a preferred method, the retaining clamp 18 can be slid onto the proximal end of the catheter 12, which is then lubricated. Prior to inserting the lubricated catheter 12 the clamp 18 is slid to the distal end of the catheter and locked in place by tightening the thumb screw 32. The catheter 12 is then inserted into the urinary tract and thence into the bladder. After the bladder has been emptied, the thumb screw is loosened, the retaining clamp is slid in a proximal direction until it comes in contact with the meatus, after which it is retightened and locked onto the catheter.

Figure 4:
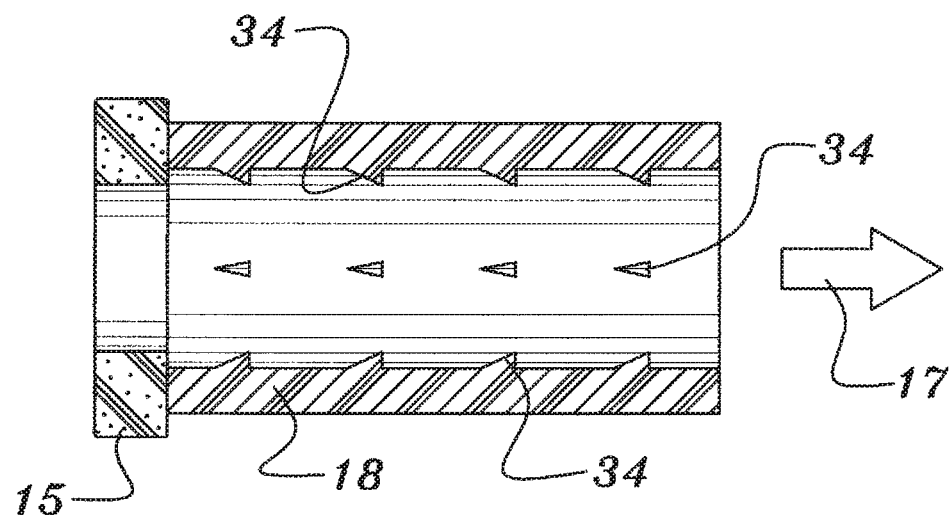
FIG. 4 is a cross-sectional view of a second embodiment of a clamping member.

In another embodiment the clamp 18 comprises a tubular member that easily slides along the catheter from a distal point to a proximal one but that resists sliding in a distal direction. A clamp of this sort may have an array of slanted teeth 34, or other asymmetric frictive elements disposed on its inner surface. A schematic depiction of such a clamp appears in FIG. 4 where the direction of easy motion is indicated by a white arrow 17.

The skilled reader will recognize that although preferred embodiments of the retaining clamp are solid bodies having a throughhole through which the catheter passes, this is not a defining characteristic. Many other configurations, including those comprising grooved bodies clamped about an installed catheter, can be considered.

Although the present invention has been described with respect to several preferred embodiments, many modifications and alterations can be made without departing from the invention. Accordingly, it is intended that all such modifications and alterations be considered as being within the spirit and scope of the invention as defined in the attached claims.

The invention claimed is:

1. An apparatus for retaining a portion of a urinary catheter in a male patient, the apparatus comprising:
   a clamp member comprising a sleeve having an inner diameter greater than an outer diameter of the catheter, the clamp member slidable along the catheter and affixable thereto adjacent a meatus of the male patient's penis;
   an anchor member comprising a fabric having hook-and-loop bonding portions, the fabric configured to be wrapped around a shaft of the penis; and
   at least one elongate linking member having two ends respectively bonded by hook-and-loop fasteners to the clamp member and to the anchor member.

2. The apparatus of claim 1 wherein the clamp member further comprises a thumb screw threaded into the sleeve.

3. The apparatus of claim 1 wherein the anchor member has an outer diameter less than a diameter of a corona of the patient's penis.

4. An apparatus for retaining a portion of a urinary catheter in a male patient, the apparatus comprising:
   a clamp member comprising a sleeve and a thumb screw threaded thereinto, the clamp engaging the catheter so as to prevent relative motion between the clamp member and the catheter, the clamp member comprising a hook-and-loop bonding portion;
   an anchor member comprising a flexible sheet configured to be wrapped about a shaft of the male patient's penis to form a tubular anchor having a hook-and-loop bonding portion on an external surface thereof; and
   at least one link member extending between the clamp member and the anchor member, the link member bonded to both the clamp member and the anchor member by a hook-and-loop fastener.

5. The apparatus of claim 4 wherein the tubular anchor has an outer diameter less than a diameter of a corona of the patient's penis.

6. A method of retaining a proximal portion of a urinary catheter in a male patient, the method comprising the steps of:
   a) attaching an anchor member around the shaft of the patient's penis, the anchor member comprising a hook-and-loop bonding portion;
   b) sliding a clamp member comprising a sleeve and a thumb screw along a distal portion, external of the patient, of the catheter from a more distal location to a more proximal location adjacent the patient's meatus, and turning the thumb screw to fixedly attach the clamp member to the catheter, the clamp member comprising a hook-and-loop bonding portion; and
   c) attaching, by means of a linking member having at least one hook-and-loop bonding portion, the clamp member to the anchor member so as to hold the clamp member against the patient's penis.

7. The method of claim 6 wherein the step of attaching the clamp member to the anchor member is carried out subsequent to steps a) and b).

\* \* \* \* \*